United States Patent [19]
Varisco

[11] Patent Number: 5,265,149
[45] Date of Patent: Nov. 23, 1993

[54] ANTI-TOPPLING MOBILE RADIOLOGY STAND WITH RESTRICTIVE UNFOLDING

[75] Inventor: Piero Varisco, Villasanta Milano, Italy

[73] Assignee: General Electric CGR S.A., Issy les Moulineaux, France

[21] Appl. No.: 913,921

[22] Filed: Jul. 17, 1992

[30] Foreign Application Priority Data

Jul. 19, 1991 [FR] France .................. 91 09186

[51] Int. Cl.⁵ .......................................... H05G 1/02
[52] U.S. Cl. .................................... 378/198; 378/195; 378/193
[58] Field of Search ............... 378/198, 197, 193, 196, 378/195

[56] References Cited

U.S. PATENT DOCUMENTS

| | | | |
|---|---|---|---|
| 4,326,131 | 4/1982 | Waerve | 378/198 |
| 4,964,151 | 10/1990 | Trotel | 378/198 |
| 4,989,229 | 1/1991 | Negrelli et al. | 378/198 |
| 5,081,662 | 1/1992 | Warden et al. | 378/198 |

FOREIGN PATENT DOCUMENTS

2175841 10/1973 France .
2405612 5/1979 France .
2405695 5/1979 France .

*Primary Examiner*—Paul M. Dzierzynski
*Assistant Examiner*—Kim-Kwok Chu

[57] ABSTRACT

A mobile radiology machine that meets anti-toppling standards is made by limiting the unfolding of the structure that holds the X-ray tube, so that this unfolding occurs as a function of the angle of orientation of this structure about a vertical axis of exploration. It is shown that, under these conditions, it is possible to obtain satisfactory operation from a mobile radiology machine that weighs less and can be moved, if necessary, without the use of motors.

20 Claims, 4 Drawing Sheets

FIG_1
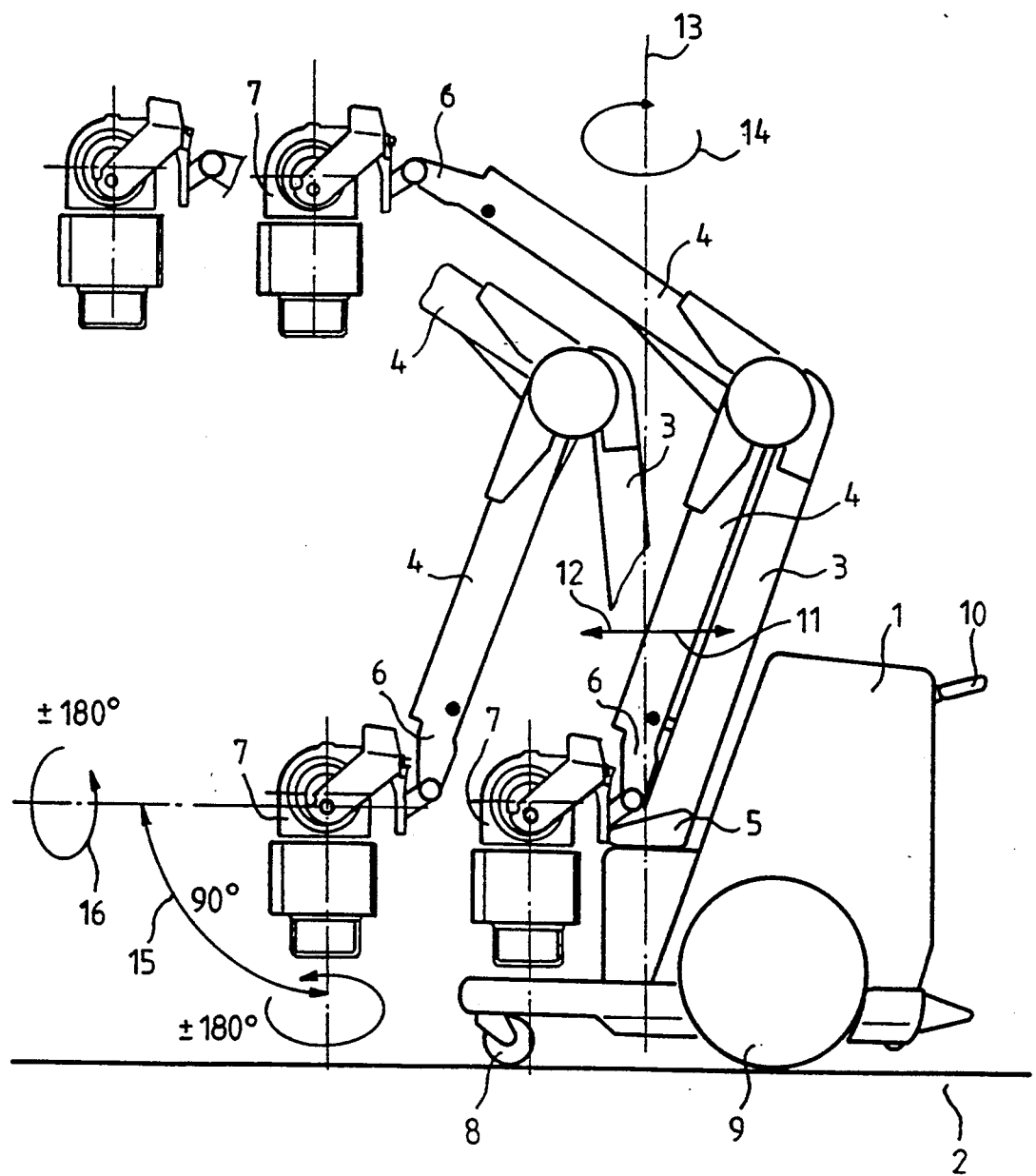

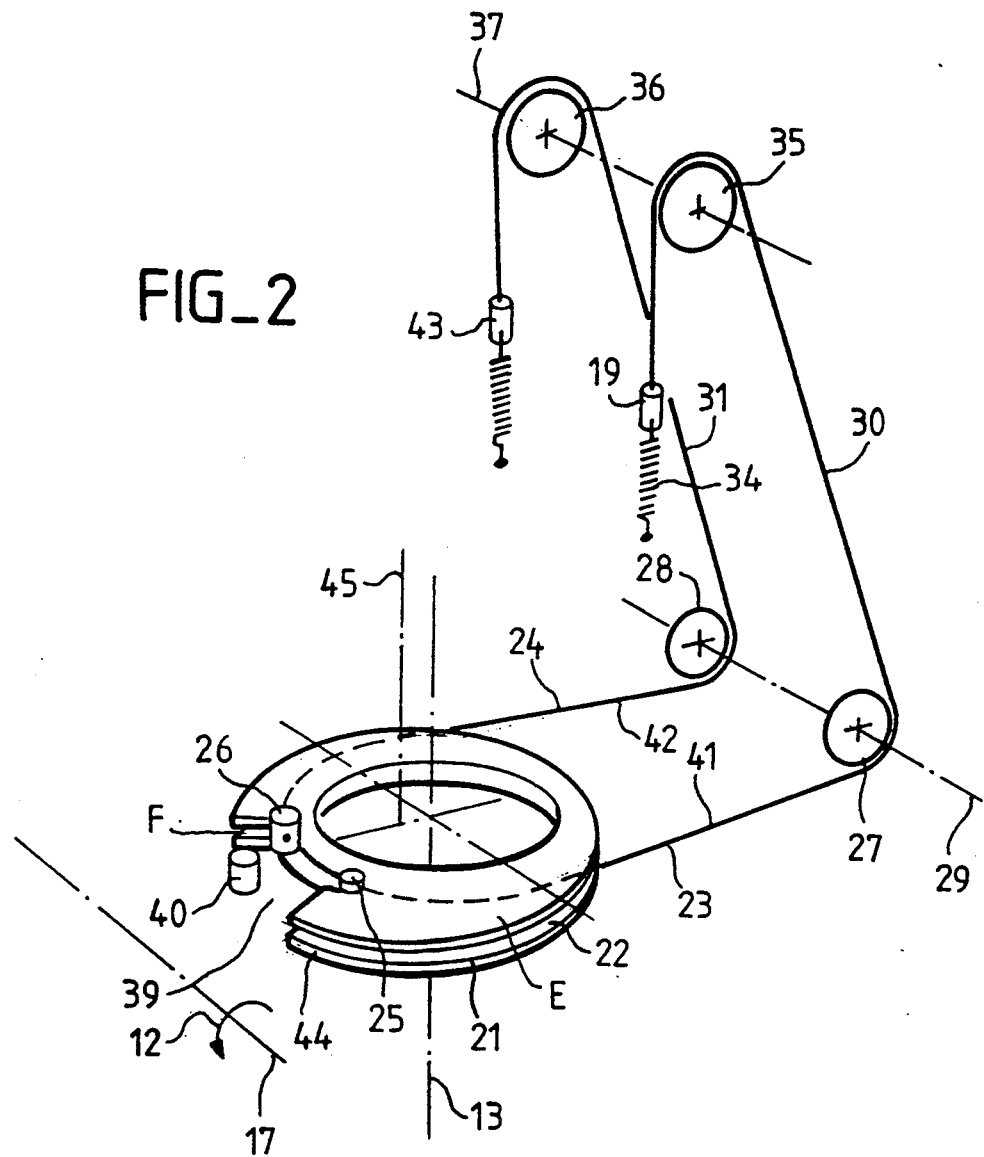
FIG_2

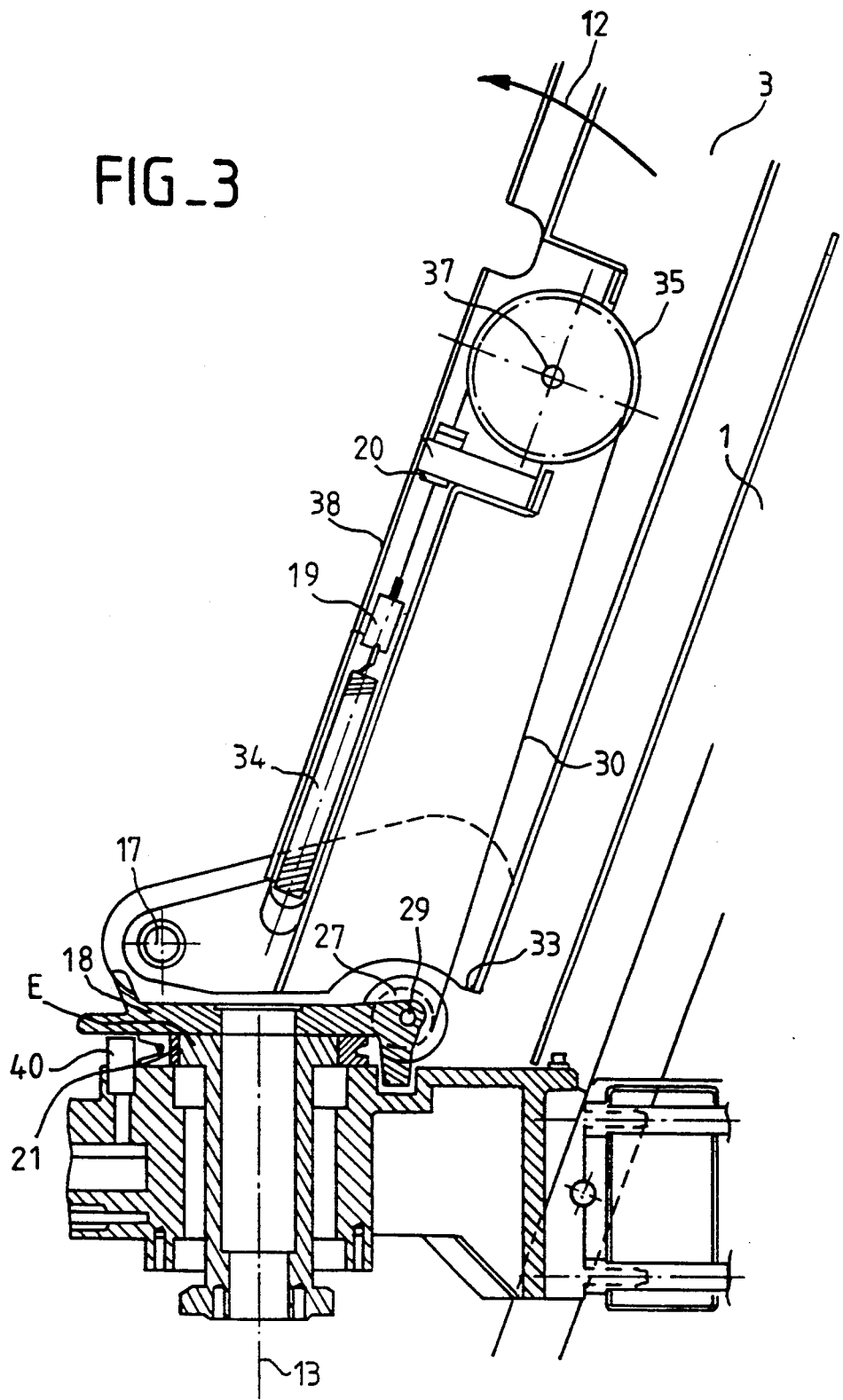

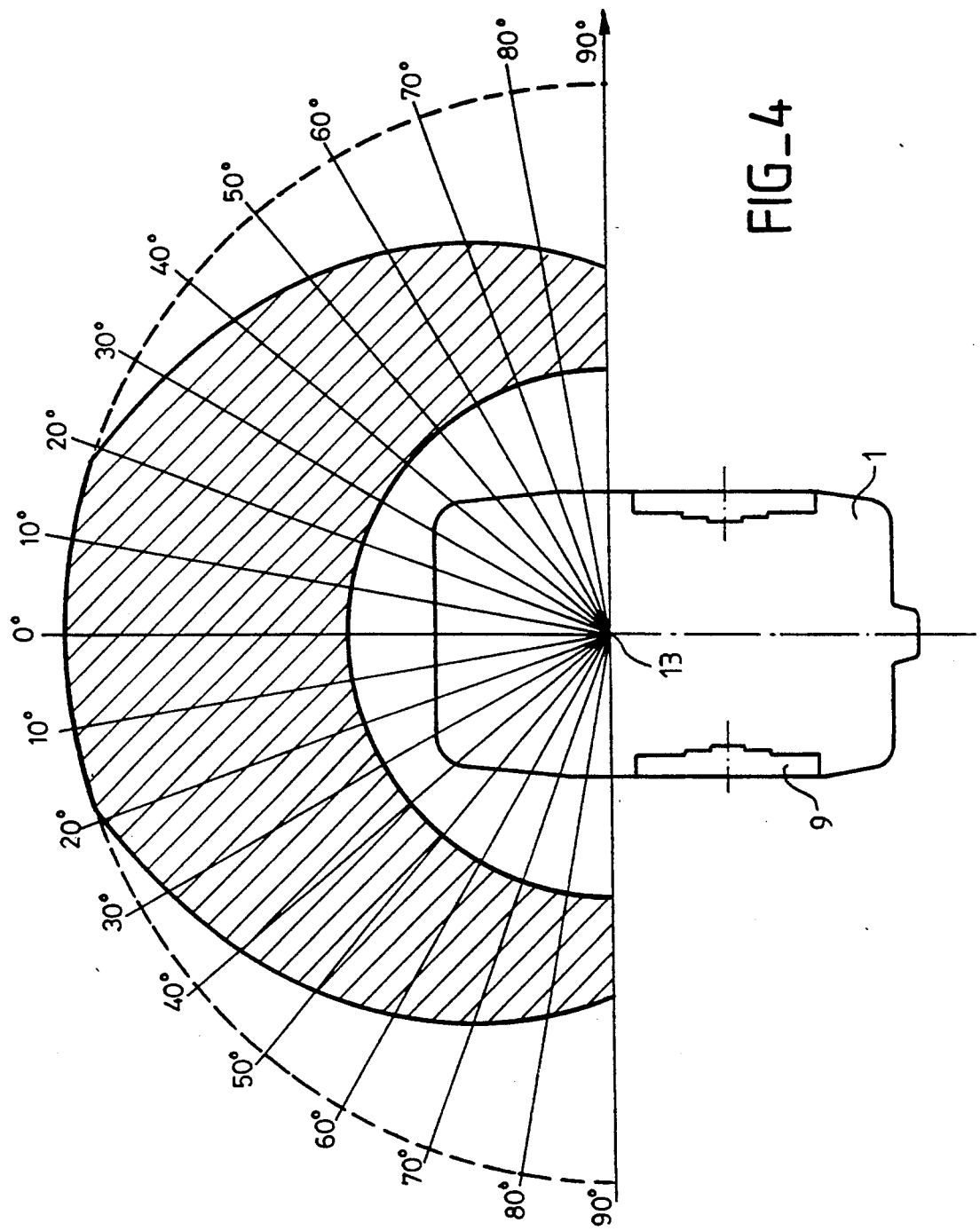

ANTI-TOPPLING MOBILE RADIOLOGY STAND WITH RESTRICTIVE UNFOLDING

BACKGROUND OF THE INVENTION

1. Field of the Invention

An object of the present invention is a mobile radiological machine that can be used chiefly in the field of medicine. A mobile radiological machine is a radiological machine that bears an X-ray tube and can be used to bring this X-ray tube to the vicinity of a patient in any position and at any angle. A mobile machine such as this make's it possible notably to take radiographs of patients when it is impossible to bring them to a conventional type of radiography table because their health does not permit it.

2. Description of the Prior Art

There are known mobile radiological machines constituted by a carriage that has a rectangular seating and supports a structure of hinged arms, to the end of which the X-ray tube is fixed. During use, the structure of arms is unfolded and the X-ray tube is presented in a projecting position with respect to the seating of the carriage. It can thus be shifted to the front or to the sides of the carriage. There are standards of stability that these mobile radiological machines must meet. For example in a test where it is sought to overturn the carriage by the application of a 23 kg effort to the X-ray tube, this effort should be countered effectively for any position of the carriage. To meet these constraints, mobile radiological machines of very great weight are built. For example, there are known mobile radiological machines with a total weight of the order of 450 kg. These machines are so heavy that they can be moved only by means of motors.

In the invention, it is sought to reduce the weight of a mobile radiological machine of this type in order to be able, if necessary, to remove the motors while at the same time also meeting the anti-toppling standards.

To resolve these problems, in the invention, the structure with unfolding arms has been provided with a unfolding limiting mechanism that takes account of the rectangular character of the carriage. Indeed, when the arm is unfolded towards the front of the carriage, since the carriage is long, the arms may be stretched further than when its arms extend laterally with respect to the carriage since the carriage is less wide than it is long. Consequently, the frontward overturning moment should be greater, for a given unfolding, than the sideways overturning moment.

Consequently, it is possible to allow greater unfolding towards the front. Consequently, in the invention, the mobile machine has been provided with means by which the unfolding of the structure is a function of the angle of orientation of this unfolding. The unfolding is the maximum towards the front and is limited on the sides.

SUMMARY OF THE INVENTION

An object of the invention is a mobile radiological machine comprising a carriage that is mobile on the ground, an unfolding structure that is mechanically connected to the carriage by a first end and to an X-ray tube (7) by its second end, the structure being capable of being unfolded in a projecting position with respect to the carriage and being capable of rotating about a vertical axis, wherein said machine comprises means so that the maximum amplitude of the unfolding is a function of the angle of rotation of this structure about the vertical axis.

BRIEF DESCRIPTION OF THE DRAWINGS

The invention will be understood more clearly from the following description and from the appended drawings, which are given purely by way of an indication and in no way restrict the scope of the invention. Of the FIGURES:

FIG. 1 shows a mobile radiological machine provided with the anti-toppling device of the invention;

FIG. 2 shows a preferred exemplary embodiment of the anti-toppling mechanism of the invention;

FIG. 3 shows details of an embodiment of the mechanism of FIG. 2;

FIG. 4 shows a schematic view of the tolerances of access in space with the X-ray tube of the mobile machine of the invention.

MORE DETAILED DESCRIPTION

FIG. 1 shows a mobile radiological machine that can be provided with the anti-toppling device of the invention. The mobile machine essentially comprises a carriage 1 that is mobile on the ground 2 and bears a unfolding structure including arms 3, 4, represented herein in several positions of unfolding. The unfolding structure is fixed by a first end 5 to the carriage and, at its second end 6, to an X-ray tube 7 as well as all the logistical means that are associated with this tube and are necessary to make it work. The carriage has a front part provided with small swivelling wheels or casters 8 and a rear part borne, on each side, by two big wheels 9. Only one side of the mobile machine is seen in the FIGURE. To be shifted, the carriage also has a handle 10.

Apart from the movements of the carriage on the ground 2, the unfolding structure may be made mobile in several ways. Firstly, it can undergo a first motion represented by the arrows 11 and 12, by which its structure gets unfolded in projecting position rearwards and frontwards with respect to the seating of the carriage 1. Thus, with the exception of the parking position in which the tube 7 is brought to the vicinity of the end 5, in the cases shown the position straight below the X-ray tube is beyond the front wheels 8. There then exists a natural toppling moment, frontwards, which increases with the size of the projection. However, since all the control circuits are kept in the rear of the carriage, their weight exerts a natural moment of reaction.

The unfolding structure may furthermore accept a second motion: a rotational motion about a vertical axis 13 indicated by the arrow 14. In one example this motion is restricted mechanically, on each side of the main direction of the carriage measured along its length at ±90°. It shall be seen hereinafter that, given the rectangular character of the carriage, the extension of unfolding is no longer as great on the sides as it is towards the front to meet the same anti-toppling standards, given the small weight chosen for the carriage. Finally, the X-ray tube 7 may itself be subjected to two motions: a first motion 15 by which the angle of incidence can be made to vary and a second motion 16 by which the field of detection can be oriented if a rectangular type of detection field should be taken. The latter two motions are optional. What counts is the measurement of the projection of the tube 7 with respect to the base of the carriage 1.

FIG. 2, in common with FIG. 3, shows a preferred manner of operation of the anti-toppling mechanism of the invention. The end 5 of the structure 3-4 is hinged on a horizontal rotational axis 17 perpendicular to the plane of FIG. 3 seen in a sectional view. Consequently, the first arm 3 of the structure may tilt frontwards about the axis 17. During this frontward tilting, its inclination changes. This inclination is measured by the device of the invention, at the same time as the rotational position of the base 18 about the axis 13.

In the preferred exemplary embodiment of the invention, the base 18 is positioned on a loose or idle pulley 21 which itself may also rotate about the axis 13. This idle pulley has a groove 22 within which one or more cables are fixed, at least at one position. For example, two cables 23 and 24 are partially wound in the groove and are fixed by their ends, respectively 25 and 26, so that they cannot slide at the bottom of this groove. Rather than having two cables, it is possible to have a continuous cable which, in this case, would be fixed in a single position at the bottom of the groove 22. FIG. 2 also shows the axis 17 as well as the motion 12 of variation of the inclination. The axis 17 is orthogonal to the axis 13: it is placed slightly towards the front of the carriage, towards the small wheels. The cables 23 and 24 furthermore pass over guide pulleys, respectively 27 and 28, which may rotate about another horizontal axis, called a guide axis 29. The axis 29 is also borne by the base 18. This can also be seen in FIG. 3.

When the arm 3 is inclined frontwards, strands 30 and 31 of the cable 23 move inside this arm 3. They move therein because the arm 3 pivots about the axis 17. The result thereof is that the rear end 33 of the arm 3 moves away from the pulleys 27 and 28 and from the guide axis 29. Since the axis 29 is fixed horizontally, the strands 30 and 31 descend towards the arm 3 when this arm 3 is inclined frontwards. When the strands 30 and 31 descend, movable stops such as 19 rise towards fixed stops such as the stop 20. The stop 20 is fastened to the arm 3. The stop 19 is fastened, firstly, to the end of the strand 30 of the cable 23 and, secondly, to an end of spring 34, the other end of which is furthermore fixed to the arm 3 or to the base 18. The stop 19 herein takes the shape of a sleeve mounted on the cable 23. The place at which the second end of the spring 34 is fixed is not important. What counts is that the cable 23 and the strands 30 and 31 are, firstly, held at the bottom of the grooves and, secondly, tensioned in the arm 3.

The sliding motion of the arm 3, and of the strands 30 and 31 in the arm 3, prompts rising movements of the mobile stops 19 owing to the presence, by way of an improvement, of so-called "presentation" pulleys 35 and 36 rotating about a so-called horizontal "presentation" axis 37. The axis 37 is fixed to the arm 3. The justification for the pulleys 35 and 36 lies in the fact that a window 38 is made in the arm 3 for achieve the heightwise adjustment of the position of the fixed stop 20. This fixed arm is, for example, hollow: the cable 23 goes through it. As the lengths of the cables 23 or 24 may vary according to their manufacture, the drawback entailed by the fact that these lengths are not constant is overcome by adjusting the height of the stop 20. The stop 20 is, for example, provided with an external thread: it is screwed to varying depths into a support that holds it in the arm 3. If the window 38 had not been made towards the front of the arm 3, there would have been no need for the pulleys 35 and 36. However, in this case, the window 38 would have been located towards the rear of the arm 3, at a position where it would have been liable to be handled when the arm 3 was being pushed forward by hand. The presence of this window would have then been dangerous.

We have seen how, when the arm 3 is inclined frontwards, the stop 19 comes into contact with the stop 20. When it is in contact, it is no longer possible to incline the arm 3 frontwards. We shall now show how the height of the stop 19 can be adjusted as a function of the rotation of the unfolding structure and hence of the arm 3 about the vertical axis 13. When this structure rotates, the idle pulley 21 is driven by friction: it rotates with the base 18. Or else it is driven by the reaction of one of the mobile stops on the corresponding fixed stop.

The idle pulley 21 is provided with a notch 39 within which there is engaged a pivot 40. The pivot 40 is fixedly joined to the carriage 1. The pivot 40 is fixed when the structure rotates. Consequently, when an edge of the notch comes into contact with the pivot 40, the idle pulley 21 can no longer rotate: it is stopped. At this instant, if the structure continues to be made to rotate, the base 18, driving the axis 29 with it, shifts the pulleys 27 and 28 in a horizontal plane. Under these conditions, a cable 41 of the cable 23, which goes from the pulley 27 to the pulley 21, gets wound in the groove 22 of the pulley 21. On the other side, a strand 42 of the cable 24 gets unwound from the pulley 21. Since the cable 41 gets wound, the stop 19 rises (FIG. 2). In other words, for a motion in the trigonometrical sense, the mobile stop 19 rises: it is this mobile stop which, as a function of value of the orientation, fixes the height of the limit of tilt. In the event of clockwise rotation, it is the height of the other mobile stop 43 that fixes the limit of the tilt.

In other words, if the structure is folded, and if it is made to rotate about the axis 13, the mobile stops 19 and 43 get locked in terms of height according to the angle of orientation of the structure. If, subsequently, it is desired to tilt the arm 3 frontwards, this is prevented by the first of these mobile stops which comes into contact with one of the fixed stops of the arm 3.

By contrast, if the structure is unfolded entirely frontwards, with zero orientation, and if the structure is then made to rotate about the axis 13, the rising of one of the mobile stops 19 or 43 prompts an automatic folding as a function of the angle of rotation.

This is shown schematically in FIG. 4. The carriage 1 as well as its big wheels 9 are seen. The structure is not shown, but the tolerated positions directly below the X-ray tube 7 with respect to the axis 13 have been indicated in the hatched zone. Towards the front, when the orientation is 0°, the unfolding is the maximum. When orientations of the order of 20° are reached, the unfolding is gradually reduced: it no longer follows the arc of a circle shown in dashes but, on the contrary, gets gradually reduced.

To obtain the permitted sector of the motion of the idle pulley E in a simple way, the notch 39 is made as follows. The bottom of the groove 22 is round and is machined in taking, as the center of curvature, the axis 13 about which the pulley has to rotate. By contrast, the tops 44 of the groove 22 are, for their part, also rounded but centered on a vertical axis that is offset with respect to the axis 13. For example, an axis 45 is offset by one cm from the axis 13. In other words, the external edge of the grooves is off-centered with respect to the bottom of the grooves. In the widest off-centered part, it is then possible to cut out a notch 39. The machining is very simple. The notch could have been replaced by any system of catches welded to the pulley or even possibly the pivot 40 could have been made differently.

What is claimed is:

1. A mobile radiological machine comprising: a carriage that is mobile on the ground, an unfolding structure that is mechanically connected, at a first end thereof, to the carriage and to an X-ray tube as its second end, the structure being capable of being unfolded in a projecting position with respect to the carriage and being capable of rotating about a vertical axis, wherein said machine further comprises means for limiting the maximum amplitude of unfolding as a function of the angle of rotation of this structure about the vertical axis.

2. A mobile radiology machine according to claim 1, wherein the structure further comprises: a first arm that is mechanically connected, at its first end, to the carriage and at its second end to a first end of a second arm, the second arm being connected at its second end to the X-ray tube, the first arm being capable of being inclined with respect to the vertical and being capable of rotating about the vertical axis, and means for limiting the maximum angle of inclination of the first arm as a function of the angle of rotation of this first arm about the vertical axis.

3. A mobile radiological machine comprising:
a carriage that is mobile on the ground, an unfolding structure that is mechanically connected, at a first end thereof, to the carriage and to an X-ray tube at its second end, the structure being capable of being unfolded in a projecting position with respect to the carriage and being capable of rotating about a vertical axis, wherein said machine further comprises means for limiting the maximum amplitude of unfolding as a function of the angle of rotation of this structure about the vertical axis;

the structure further including a first arm that is mechanically connected, at its first end, to the carriage and at its second end to a first end of a second arm, the second arm being connected at its second end to the X-ray tube, the first arm being capable of being inclined with respect to the vertical and being capable of rotating about the vertical axis, and means for limiting the maximum angle of inclination of the first arm as a function of the angle of rotation of this first arm about the vertical axis;

and further wherein the means to make the inclination a function of the rotation comprise a set of mobile stops, the locking of the stops being a function of the rotation, said mobile stops coming into contact with fixed stops when the inclination has to be prevented.

4. A mobile machine according to claim 3, wherein the means to make the inclination a function of the rotation comprise an idle pulley that rotates about the vertical axis, the rotation of the idle pulley being limited to a sector, two cables each passing through the pulley, one of the ends of each cable being fixedly connected to the pulley, and the other end of each cable being connected to a mobile stop, the positions of each mobile stop being locked by winding the cables about the idle pulley.

5. A mobile machine according to claim 4, wherein the first arm can be tilting about a horizontal axis of inclination, positioned on a base rotating about the vertical axis, the cables passing through guide pulleys which rotate about a horizontal guide axis, the guide axis being also positioned on the rotating base, these two horizontal axes being placed on each side of the vertical axis, the mobile stop shifting in relation to the first arm when this first arm is inclined.

6. A mobile machine according to claim 5, wherein the first arm comprises presentation pulleys to send on a device for the adjusting of fixed stops on one of the faces of the first arm.

7. A mobile machine accorder to claim 5, wherein, to limit the rotation of the idle pulley to a sector, this idle pulley has a notch, and wherein a pivot fixedly joined to the carriage is engaged in this notch.

8. A mobile machine according to claim 4, wherein the first arm comprises hollow fixed stops through which there pass the cables, two mobile stops fixedly joined to the ends of the cables being shifted during the rotation, for their locking, by the action of two springs fixed under tension to the ends of the cables.

9. A mobile machine according to claim 4, wherein the first arm comprises presentation pulleys to send on a device for the adjusting of fixed stops on one of the faces of the first arm.

10. A mobile machine according to claim 4, wherein, to limit the rotation of the idle pulley to a sector, this idle pulley has a notch, and wherein a pivot fixedly joined to the carriage is engaged in this notch.

11. A mobile radiological machine comprising:
a carriage that is mobile on the ground, an unfolding structure that is mechanically connected, at a first end thereof, to the carriage and to an X-ray tube as its second end, the structure being capable of being unfolded in a projecting position with respect to the carriage and being capable of rotating about a vertical axis, wherein said machine further comprises means for limiting the maximum amplitude of unfolding as a function of the angle of rotation of this structure about the vertical axis;

the structure further including a first arm that is mechanically connected, at its first end, to the carriage and at its second end to a first end of a second arm, the second arm being connected at its second end to the X-ray tube, the first arm being capable of being inclined with respect to the vertical and being capable of rotating about the vertical axis, and means for limiting the maximum angle of inclination of the first arm as a function of the angle of rotation of this first arm about the vertical axis;

and further wherein the means to make the inclination a function of the rotation comprise an idle pulley that rotates about the vertical axis, but the rotation of the idle pulley is limited to a sector, a cable passing through the pulley, a part of this cable being fixedly connected to the pulley, at least one end of this cable being connected to a mobile stop, the position of this mobile stop being locked by winding the cable about the idle pulley.

12. A mobile machine according to claim 11, wherein the first arm can be inclined by tilting about a horizontal axis of inclination, positioned on a base rotating about the vertical axis, the cable passing through a guide pulley which rotates about a horizontal guide axis, the guide axis also being positioned on the rotating base, these two horizontal axes being placed on each side of the vertical axis, the mobile stop shifting in relation to the first arm when this first arm is inclined.

13. A mobile machine according to claim 12, wherein the first arm comprises hollow fixed stops through which there pass the cable two mobile stops fixedly joined to the ends of the cable being shifted during the rotation, for their locking, by the action of two springs fixed under tension to the ends of the cable.

14. A mobile machine according to claim 12, wherein the first arm comprises presentation pulleys to send on a device for the adjusting of fixed stops on one of the faces of the first arm.

15. A mobile machine according to claim 12, wherein, to limit the rotation of the idle pulley to a sector, this idle pulley has a notch, and wherein a pivot fixedly joined to the carriage is engaged in this notch.

16. A mobile machine according to claim 11, wherein the first arm comprises hollow fixed stops through which there pass cables, two mobile stops fixedly joined to the ends of the cables being shifted during the rotation, for their locking, by the action of two springs fixed under tension to the ends of the cables.

17. A mobile machine according to claim 16, wherein, to limit the rotation of the idle pulley to a sector, this idle pulley has a notch, and wherein a pivot fixedly joined to the carriage is engaged in this notch.

18. A mobile machine according to claim 11, wherein the first arm comprises presentation pulleys to send on a device for the adjusting of fixed stops on one of the faces of the first arm.

19. A mobile machine according to claim 11, wherein, to limit the rotation of the idle pulley to a sector, this idle pulley has a notch, and wherein a pivot fixedly joined to the carriage is engaged in this notch.

20. A mobile machine according to claim 11, wherein the idle pulley possesses a groove, the round bottom of which is centered on a first vertical axis and the upper round edges of which are centered on a second vertical axis, offset with respect to the first vertical axis.

* * * * *